United States Patent [19]

Beck et al.

[11] Patent Number: 4,664,668
[45] Date of Patent: May 12, 1987

[54] HIP JOINT PROSTHESIS

[75] Inventors: Heinrich Beck, Erlangen; Karl M. Richter, Wendtorf, both of Fed. Rep. of Germany

[73] Assignee: Howmedica International, Inc., Kiel, Fed. Rep. of Germany

[21] Appl. No.: 722,938

[22] Filed: Apr. 12, 1985

[30] Foreign Application Priority Data

Apr. 14, 1984 [DE]  Fed. Rep. of Germany ... 8411765[U]

[51] Int. Cl.$^4$ ................................................. A61F 2/32
[52] U.S. Cl. ...................................................... 623/23
[58] Field of Search ......................... 128/92 C, 92 CA; 623/18, 19, 20, 21, 22, 23

[56] References Cited

U.S. PATENT DOCUMENTS

| 3,658,056 | 4/1972 | Huggler et al. | 623/22 |
| 3,996,625 | 12/1976 | Noiles | 623/22 |
| 4,040,129 | 8/1977 | Steinemann et al. | 128/92 C |
| 4,153,953 | 5/1979 | Grobbelaar | 623/23 |
| 4,355,428 | 10/1982 | Deloison et al. | 623/16 |
| 4,406,023 | 9/1983 | Harris | 623/22 |
| 4,430,761 | 2/1984 | Niederer et al. | 3/1.91 |

FOREIGN PATENT DOCUMENTS

| 32165 | 12/1983 | European Pat. Off. | 623/23 |
| 98224 | 1/1984 | European Pat. Off. | 623/23 |
| 837294 | 4/1952 | Fed. Rep. of Germany | 128/92 CA |
| 3216539 | 11/1983 | Fed. Rep. of Germany | 623/22 |
| 2538242 | 6/1984 | France | 623/23 |

Primary Examiner—Richard J. Apley
Assistant Examiner—David Isabella
Attorney, Agent, or Firm—Charles J. Knuth; Peter C. Richardson; Lawrence C. Akers

[57] ABSTRACT

A hip joint prosthesis comprises a femoral component having an elongated shank formed of a metal alloy and a joint head adapted to cooperate with the natural acetabulum or a prosthetic acetabulum likewise formed of a metal alloy. The shank has approximately the same width in the lateral-medial plane and a slightly downwards tapered width in the anterior-posterior plane.

9 Claims, 11 Drawing Figures

HIP JOINT PROSTHESIS

BACKGROUND OF THE INVENTION

The present invention relates to a hip joint prosthesis comprising a femoral component having a shank formed of a metal alloy and a joint head, said joint head adapted to cooperate with either the natural acetabulum or a prosthetic acetabulum likewise formed of a metal alloy.

The basic construction of the femoral portion of a hip joint endoprosthesis is typically the same. The shank is anchored with or without bone cement in the proximal femoral canal. A radially projecting collar serves as an abutment for limitng the extent of insertion during impaction. The joint head is typically formed by a joint ball formed integrally with the shank or by a separate joint ball fastened at the neck of the femoral component. The joint head for its part cooperates with the natural acetabulum or a prosthetic acetabulum. It is known to design the prosthetic acetabulum to be bipartite, with a preferably metallic outer portion anchored in the hip bone, while a flexible inner portion accommodated by the outer portion accommodates the joint head in snapping engagement.

It is known to anchor the prosthesis shanks in the femur canal with the aid of bone cement. As the danger exists that after a longer period of time a loosening may occur between the prosthesis shank and the bone cement due to constant dynamic load, it has already been proposed to fasten the prostheses without bone cement by positively accommodating the femur shank in the femur canal. This may be carried out, for instance, with the aid of a relatively long shank.

SUMMARY OF THE INVENTION

The invention is based upon the problem of providing a hip joint endo-prosthesis, the metallic member of which may be connected still more effectively to the apertaining bone.

In accordance with the invention this object is obtained in that the shank has approximately the same width in the lateral medium plane and in the anterior posterior plane tapers slightly downwards.

It has been found that a prosthesis shank extending in such a way may be positively anchored in the femur canal particularly effectively, above all, if, in accordance with a further embodiment of the invention the shank is elongated over the major portion of its length—beginning at the distal end—and has an approximately uniform cross-sectional area.

According to another embodiment of the invention the cross-ectional area of the shank is approximately square with rounded longitudinal edges. The longitudinal edges are preferably strongly rounded, in order to reduce a notching effect in this region. Such a shank profile has a relatively high moment of intertia with respect to all axes and, in addition, secures the shank against twisting.

According to another embodiment of the invention there are protuberances formed on the outer surface of the shank. These protuberances, according to another embodiment of the invention are circular in cross section and have a height slightly less than the diameter. The circular protuberances are rounded at the edges thereof, so that no sharp edges are formed. They are in turn spaced from each other through a distance slightly less than the outer diameter. It is possible with the aid of such a surface of the shank effectively to anchor the latter in the femur canal, with the protuberance allowing a "growing-in" of tissue. But nevertheless, the protuberances have no obstructive effect in the process of beating-in. The diameter thereof is about 2 mm with a height of 1.2 mm.

The shank of the prosthesis according to the invention, in a further development thereof, is preferably formed with protuberances on the lateral and medial sides of the shank. The anterior and posterior sides of the shank, according to another embodiment of the invention, are formed with parallel grooves. The grooves, according to a further development, are preferably arranged so close to each other that a tooth profile will form in cross section.

In another embodiment of the invention, provision is made for the shank and/or the prosthetic acetabulum to be cast of a titanium alloy containing iron and aluminum. The alloy preferably is $TiAl_5Fe_{2.5}$. Such an alloy is extremely compatible with tissue and in addition has an elasticity modul which is substantially smaller than with conventional alloys. In the case of the preferred embodiment the E-modul only is half as great. Owing to this, the elasticity of the prosthesis shank, for instance, approaches that of the bone, so that the extent of relative movements between bone and prosthesis in case of a dynamic load is reduced. As a result thereof, also the load on the prosthesis in view of a loosening of the anchoring thereof in the bone is reduced.

In order to fix the radial position of the shank provision is made in another embodiment of the invention for a wing-like extension to be integrally formed laterally at the proximal portion of the shank. The wing-like extension prevents a rotation of the shank. In another embodiment of the invention, it is provided with an elongated opening. It is possible in case of a reoperation to extract the femoral portion of the endoprosthesis via this opening. But the opening also enables tissue to grow through and thus an improved anchoring of the shank in the bone.

As already mentioned, prosthetic acetabula frequently are designed to be bipartite with an outer metallic cup and an inner cup preferably consisting of synthetic material for the accommodation of the joint head. In this connection, provision is made in an other embodiment of the invention for the outer shell to have an approximately cylindrical portion with a radial, circumferentially extending collar formed integrally at the open end thereof.

In connection with a prosthetic acetabulum provision is made in another embodiment of the invention for axial grooves to be formed at the cylindrical circumference of the outer cup, preferably forming a tooth profile. The outer portion of the acetabulum is likewise used without cement and thus inserted in the prepared bone in an exactly fitting manner. The axial grooves in this arrangement serve to guide and to secure against rotation. In this connection, provision is made in another embodiment of the invention for parallel circumferential grooves to be formed at the cylindrical circumference of the outer cup which preferably form a tooth profile. The circumferential grooves are intended to prevent an extraction. The circumferential grooves in this arrangement are disposed near the collar and beneath the axial grooves. The bottom of the grooves extends approximately on the same level.

In order to impart an increase of surface also to the bottom of the outer member of the acetabulum provision is made in a further development of the invention for the bottom of the outer cup to have a series of elevations formed on the outer surface thereof, which preferably have a pyramidal configuration.

The inner member of the prosthetic acetabulum as a rule consists of synthetic material, preferably polyethylene. So that the joint ball upon insertion into the inner cup will not knock against the metallic outer cup and get damaged thereby, provision is made in another embodiment of the invention for the inner cup to have a radial flange coming to lie against the front side of the collar of the outer cup. This flange may be kept very thin, but it will take care that in case of non-centric introduction of the joint ball the latter will at most knock against the flange of synthetic material but will not get damaged thereby.

DETAILED DESCRIPTION OF THE INVENTION

The invention will be explained in more detail in the following by way of drawings.

Figure 1:
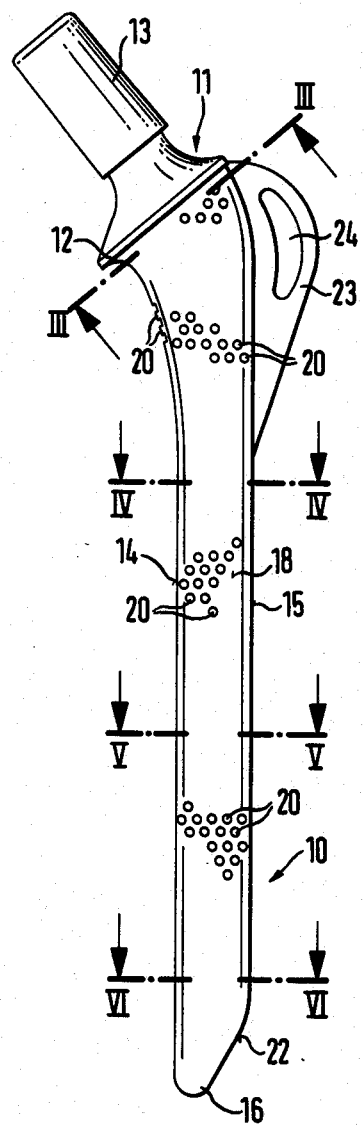
FIG. 1 shows a front view of the femoral portion of a hip joint endo-prosthesis according to the invention.

Prior to enlarging on the details shown in the drawings it has to be stated that each of the parts described by themselves or in connection with features of the claims are of inventively essential significance.

The femoral prosthesis portion shown in FIG. 1 comprises a shank 10 and a neck 11. A radial circumferentially extending collar 12 is formed between the shank 10 and the neck 11 which merges into the neck 11 via a rounded transition. It is designed to be flat on the underside. Adjoining the neck 11 is a cone 13 onto which a joint ball having a conical bore is fitted.

The femoral portion as shown preferably consists of a titanium alloy containing iron and aluminum, preferably $TiAl_5Fe_{2.5}$.

Starting from the distal end, the medial side 14 and the lateral side 15 of the shank extend approximately in parallel with respect to each other, i.e. the shank has an approximately uniform width in this plane. The lateral side 15 extends axially inwards, so that a uni-laterally tapered point 16 is formed. In the upward direction the shank enlarges in the described plane as far as the collar 13 in the shape of a wedge. At the same time it merges in a slight bend into the axial direction of the cone 13.

Figure 2:
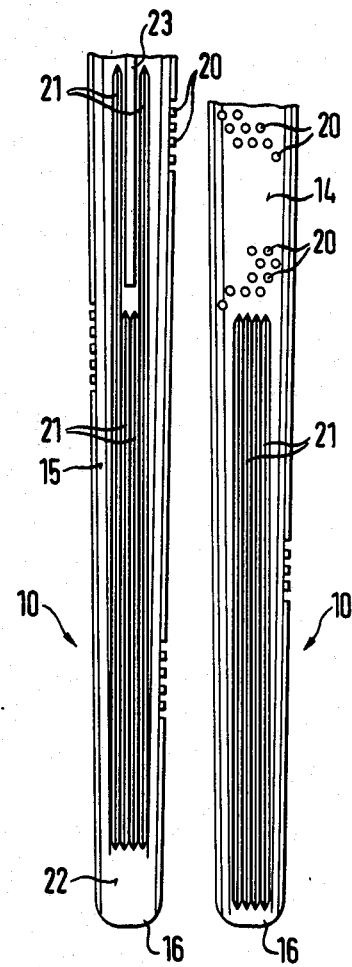
FIG. 2 shows a lateral and medial view, respectively, of the shank of the femoral portion according to FIG. 1.
Figure 3:
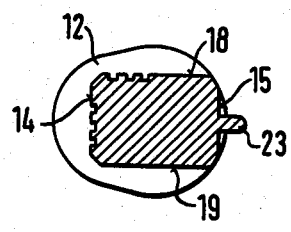
FIG. 3 shows a sectional view of the prosthesis according to FIG. 1 taken along line 3—3.

As will be recognized from FIG. 2, the shank 10 is tapered slightly in the anterior-posterior plane with a widening in the proximal direction.

Figure 5:
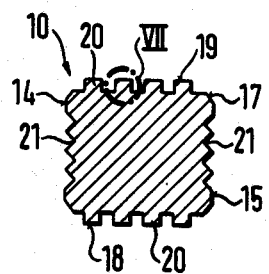
FIG. 5 shows a sectional view of the prosthesis according to FIG. 1 taken along line 5—5.
Figure 4:
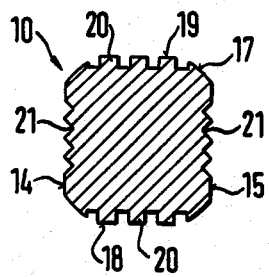
FIG. 4 shows a sectional view of the prosthesis according to FIG. 1 taken along line 4—4.
Figure 6:
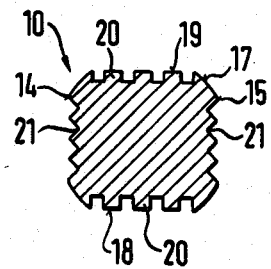
FIG. 6 shows a sectional view of the prosthesis according to FIG. 1 taken along line 6—6.
Figure 7:
FIG. 7 shows the detail 7 according to FIG. 5 on an enlarged scale.

From FIGS. 4 to 5 it will be seen that the shank 10 has an approximately square cross section over the major portion of its length with strongly rounded longitudinal edges as shown about at 17. The front side 18 and rear side 19 of the shank 10 are provided with burls 20 one of them being shown in FIG. 7 on an enlarged scale. The protuberances have a height of 1.2 mm, for example, a diameter of 2 mm and are spaced from each other through a distance of 1.75 mm. These values, however, are only exemplary but are nevertheless representing their relation to each other. The protuberances which are circular in cross section are strongly rounded at the edges and transitions, in order to avoid sharp edges.

Medially and laterally the shank 10 is provided with a series of grooves 21 triangular in cross section and extending in parallel. The grooves lie so close to each other that a uniform tooth profile is formed with the teeth triangular in cross section. On the lateral side 15 the grooves are extending as far as the oblique surface 22, while on the medial side 14 they extend approximately as far as the point 16. However, they end after three quarters of the height from the distal region. Protuberances 20 are disposed also still above the grooves 21.

On the lateral side 15 a fin-like or wing-like extension 23 is formed integrally thereat beneath the collar 12, which tapers triangularly in the distal direction following the direction of the shank 10 and in the proximal region merges arcuately to the proximal portion of the shank 10. It is provided with a likewise bent elongated opening 19. Grooves 21 respectively extend upwardly one each on either side of the extension 23, as will be seen from the lefthand representation of the FIG. 2. The ends of the grooves are configured to slope upwardly. Four grooves are formed on each side 14, 15 of the shank 10. Their width approximately covers two thirds of the areal width.

Figure 8:
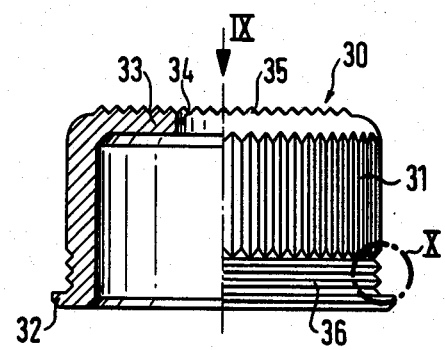
FIG. 8 shows a part sectional lateral view of the outer portion of a hip joint cup of the hip joint endoprosthesis according to the invention.
Figure 10:
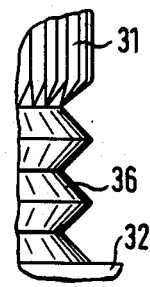
FIG. 10 shows the detail 10 of the presentation according to FIG. 8 on an enlarged scale.
Figure 9:
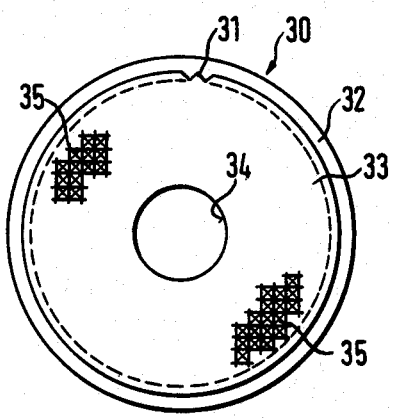
FIG. 9 shows a top plan view of the portion according to FIG. 8.
Figure 11:
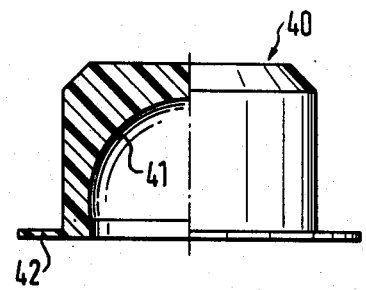
FIG. 11 shows a part sectional, part elevational lateral view of the inner portion of the hip joint cup.

The outer cup of the acetabulum according to FIGS. 8 to 10 is generally referenced 30. It consists preferably of the same material as the shank. Formed in the cylindrical jacket are a series of paraxial grooves 31, which are triangular in cross section and are arranged to lie against one another in such a manner, that triangular teeth are formed therebetween. The jacket is provided at the open side thereof with a radially outward pointing flange 32. On the opposite side a bottom 33 is formed having a central opening 34. Formed on the outer surface of the bottom 33 is a pattern of pyramidal elevations 35.

The grooves 31 terminate in front of the entry end of the outer cup 39. Formed therebetween are three circumferential grooves 36 forming between them triangular ribs or teeth. The depth of the grooves 33 corresponds to the depth of the grooves 31 as will be seen from FIG. 10. The circumferential groove 36 adjacent to the longitudinal grooves 31 is placed in such a manner that one flank of the groove is formed by the ends of the teeth between the longitudinal grooves 31 (see likewise FIG. 10). The outer cup 30 is inserted without bone cement into an opening preliminarily bored into the pelvis bone. The longitudinal grooves 31 prevent rotation, and the circumferential grooves 36 are effective to counteract extraction.

The cylindrical inner space of the outer cup accommodates an inner cup 40 of polyethylene. The inner cup 40 is selected as regards the outer dimensions thereof in such a manner that it may be fittingly inserted into the inner space of the outer cup 30. The inner cup 40 has a spherical cavity 41 to fittingly accommodate the joint ball (not shown) in snapping engagement. The inner cup 40 also has a radially outwardly pointing flange 42 at the open side thereof, which comes to lie from below against the end face and the flange 32 of the outer cup 30. The flange 42 which is made relatively thin prevents the joint ball from knocking against the metallic material when being inserted. The protuberances 20 which are uniformly distributed over the individual surfaces may be produced in a casting process or may be formed mechanically after a blank has been cast.

The design of the shaft 10 which is particularly suited for reoperations has a great volume with a favourable geometry for the production of the burls. On the lateral side 15 longitudinal grooves are better than protuberances because this side has to take the maximum load.

What is claimed is:

1. A hip joint prosthesis comprising a femoral component having a joint head and an elongated shank formed of an elastic titanium-base metal alloy having an elastic modulus comparable to that of human bone, the joint head adapted to cooperate with the natural acetabulum or a prosthetic acetabulum, the shank having a proximal end adjacent the joint head and a distal end, the shank having substantially parallel lateral and medial sides such that the width of the shank is approximately constant along substantially the entire length of the shank in the lateral-medial plane, the shank having anterior and posterior sides slightly inclined towards each other in the distal direction such that the shank is slightly tapered distally in the anterior-posterior plane, and the shank being straight and having an approximately uniform cross-section over a major portion of its length starting from said distal end, and with a multiplicity of discrete, generally cylindrically-shaped protuberances spaced from one another being provided on portions of at least the anterior, posterior and medial sides of the shank, the height of said protuberances being smaller than their diameter and the spacing between adjacent protuberances being smaller than their diameter, and said protuberances being rounded at their free ends to avoid sharp edges.

2. A prosthesis of claim 1 wherein the cross-section of the shank in said major portion is approximately a square with rounded longitudinal edges.

3. A prosthesis of claim 1 wherein a multiplicity of said protuberances are also provided on the lateral side of the shank.

4. A prosthesis of claim 1 wherein a plurality of parallel grooves are formed longitudinally on both the posterior side and the anterior side of the shank.

5. A prosthesis of claim 4 wherein said grooves lie closely proximate side-by-side together so that a sawtooth profile results in tranverse cross-sections of the shank.

6. A prosthesis of claim 1 wherein the shank is formed of a titanium-base metal alloy containing iron and aluminum.

7. A prosthesis of claim 6 wherein said alloy is $TiAl_5Fe_{2.5}$.

8. A prosthesis of claim 1 comprising additionally a fin-like extension formed integrally with the shank, said extension extending from the lateral side of the shank adjacent the proximal end of the shank and being provided with an elongated opening therein.

9. A prosthesis of claim 1 wherein the femoral component comprises additionally a radially projecting collar at the proximal end of the shank, with the angle included between the shank axis over said straight major portion of the shank and the collar being about 55°.

* * * * *